US 7,471,387 B1

(12) United States Patent
Treado et al.

(10) Patent No.: US 7,471,387 B1
(45) Date of Patent: Dec. 30, 2008

(54) SYSTEM AND METHOD FOR THE ELECTROSTATIC DETECTION AND IDENTIFICATION OF THREAT AGENTS

(76) Inventors: Patrick J. Treado, 315 South Lexington, Pittsburgh, PA (US) 15208; Charles W. Gardner, Jr., 4878 Wickloe Dr., Gibsonia, PA (US) 15044; John S. Maier, 622 S. Lang Ave., Pittsburgh, PA (US) 15208; David Keller, 353 Cambridge La., Newtown, PA (US) 18940

( * ) Notice: Subject to any disclaimer, the term of this patent is extended or adjusted under 35 U.S.C. 154(b) by 264 days.

(21) Appl. No.: 11/351,278

(22) Filed: Feb. 9, 2006

Related U.S. Application Data

(60) Provisional application No. 60/651,375, filed on Feb. 9, 2005.

(51) Int. Cl.
*G01N 21/00* (2006.01)
*G01N 21/65* (2006.01)
(52) U.S. Cl. .......................... 356/301; 356/73
(58) Field of Classification Search ................ 356/301, 356/72, 73
See application file for complete search history.

(56) References Cited

U.S. PATENT DOCUMENTS

| | | | |
|---|---|---|---|
| 4,880,052 A | 11/1989 | Meyer, IV et al. |
| 5,194,912 A | 3/1993 | Batchelder et al. |
| 5,377,004 A | 12/1994 | Owen et al. |
| 5,442,438 A | 8/1995 | Batchelder et al. |
| 5,528,393 A | 6/1996 | Sharp et al. |
| 5,539,517 A | 7/1996 | Cabib et al. |
| 5,623,342 A | 4/1997 | Baldwin et al. |
| 5,689,333 A | 11/1997 | Batchelder et al. |
| 5,710,626 A | 1/1998 | O'Rourke et al. |
| 5,862,273 A | 1/1999 | Pelletier |
| 5,866,430 A | 2/1999 | Grow |
| 5,901,261 A | 5/1999 | Wach |
| 5,911,017 A | 6/1999 | Wach et al. |
| 6,002,476 A | 12/1999 | Treado |
| RE36,529 E | 1/2000 | Lewis et al. |
| 6,717,668 B2 | 4/2004 | Treado et al. |
| 6,734,962 B2 | 5/2004 | Treado et al. |
| 6,765,668 B2 | 7/2004 | Gardner et al. |
| 6,917,423 B2 | 7/2005 | Gardner et al. |
| 6,954,667 B2 | 10/2005 | Treado et al. |

(Continued)

FOREIGN PATENT DOCUMENTS

JP 9-121889 A 5/1997

OTHER PUBLICATIONS

Caetano et al., "Evaluation of the Importance of Non-Linear Spectral Mixing in Coniferous Forests," SPIE vol. 3499, Sep. 1998, pp. 257-269.

(Continued)

*Primary Examiner*—L. G Lauchman
(74) *Attorney, Agent, or Firm*—Morgan, Lewis & Bockius LLP (57) ABSTRACT

A system and method for detecting aerosol threats comprising electrostatic collection and deposition of a threat agent onto a substrate. The threat agent deposited on the substrate is illuminated with a plurality of photons to thereby produce Raman scattered photons. The Raman scattered photons are analyzed in order to identify the threat agent.

5 Claims, 6 Drawing Sheets

U.S. PATENT DOCUMENTS 6,965,793 B2 11/2005 Treado et al.
2005/0105079 A1* 5/2005 Pletcher et al. ............... 356/72
2007/0295208 A1* 12/2007 Fairchild ....................... 95/74

OTHER PUBLICATIONS

Rasmussen et al., "Library Retrieval of Infrared Spectra Based on Detailed Intensity Information," Applied Spectroscopy, vol. 33, No. 4, Feb. 1979, pp. 371-376.

Guilment et al., "Infrared Chemical Micro-Imaging Assisted by Interactive Self-Modeling Multivariate Analysis," Applied Spectroscopy, vol. 48, No. 3, 1994, pp. 320-326.

Malinowski, Edmund R., "Factor Analysis in Chemistry," 1991, 2nd Edition, published by John Wiley & Sons, Inc. / William H. Press et al., pp. 32-82 and pp. 208-265.

* cited by examiner

SYSTEM AND METHOD FOR THE ELECTROSTATIC DETECTION AND IDENTIFICATION OF THREAT AGENTS

RELATED APPLICATION

This application claims the benefit of U.S. Patent Application No. 60/651,375 filed Feb. 9, 2005 entitled Development of a Biological Raman Electrostatic Detector Identifier (BioREDI) Sensor.

FIELD OF DISCLOSURE

This application relates generally to systems and methods for detecting and identifying hazardous agents.

BACKGROUND

Deployment of threat agents poses significant threats to both human and economic health. This threat is compounded by a limited ability to detect deployment of the agents. Prior art detection strategies rely on separate instrumentation for detection and identification of the threat agent. Conventional means of detecting airborne matter include UV-LIF and laser inducted breakdown spectroscopy. Convention means to identify a threat agent include wet chemical methods or spectroscopic methods. Identification of biological threat agents includes methods and reagents such as specific antibodies, genetic markers and propagation in culture. These identification methods are slow, labor-intensive and depend on the detection of highly-specific molecular structures. Spectroscopic means, for identification, include UV Raman spectroscopy, mass spectrometry and imaging spectrometry. UV Raman spectroscopy has limited sensitivity and specificity compared to UV Raman. Mass spectrometry is limited by significant preparation steps. Prior art imaging spectroscopy is limited by the need to switch from a broad band light source, for optical imaging, to a substantially monochromatic light source for spectroscopic imaging. This results in a signification time period between detection and identification during which time the sample may degrade.

SUMMARY

The present disclosure provides for a system and method for electrostatic depositing of a threat agent onto a substrate. The threat agent deposited on the substrate is illuminated with a plurality of photons to thereby produce Raman scattered photons. The Raman scattered photons are analyzed in order to identify the threat agent.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings:

FIG. 1 illustrates a system used in connection with the present disclosure;

FIG. 2 illustrates a device used in the system of this disclosure;

FIG. 3 illustrates a device used in the system of this disclosure;

FIG. 4 illustrates a particle produced by the system of this disclosure;

FIGS. 5A and 5B illustrate an elastic scatter image produced by the system and methods of the present disclosure; and FIGS. 6A, 6B, 6C and 6D illustrate Raman imaging analysis using the system and methods of the present disclosure.

DESCRIPTION OF THE EMBODIMENTS

Reference will now be made in detail to the embodiments of the present disclosure, examples of which are illustrated in the accompanying drawings. Wherever possible, the same reference numbers will be used throughout the drawings to refer to the same or like parts.

FIG. 1 illustrates system 100 which may be used to carry out the methods of the present disclosure. System 100 includes a deposition means 101 and a detector means 113. The deposition means may include an air intake port 104, which is open to the surrounding environment 102, a two stage electrostatic concentrator device 108, a sample 109, a deposition substrate 110 and a substrate positioning mechanism 112. The analysis means 113 comprises an optical path 119, an elastic scattering image detector 118, an illumination source 122, a spectroscopic image detector 126, a spectrometer 127 and a processor 128 having a spectral library 130.

The deposition device deposits a plurality of sample particles 109 onto the substrate 110.

In one embodiment, at least 50 sample particles are deposited onto the substrate. In another embodiment, at least about 50-250 sample particles are deposited onto the substrate. In another embodiment, at least about 250-500 sample particles are deposited onto the substrate.

With further reference to FIG. 1, system 100 uses an illumination source 122, directed along an optical path 119, with a plurality of photons to thereby produce elastic scattered photons and Raman scattered photons from the sample. The illumination source includes a low power laser.

With further reference to FIG. 1, the elastic scatter imaging detector 118 is comprised of one of the following of a CMOS detector, a CCD detector and a high frame rate digital detector. The system uses the detector 118 in combination with a feedback and control mechanism to automatically focus the sample under the collection optic. Spectroscopic detector 126 may comprise a CCD detector.

FIG. 2 illustrates the cascaded two stage Particulate Air-to-Air Electrostatic concentrator device 108. The device 108 provides for particle concentration with a low flow rate collimated output air stream. The air borne particles 102 enter the inlet port 104 at 500 liter/minute input airflow. The particles then enter the high volume concentrator 204 where the airflow is reduced by up to ten times. At the bottom 205 of the high volume concentrator excess air, 450 liter/minute, is removed from the airflow via an exit port 206. The air borne particles then enter a low volume concentrator 208 where the airflow is reduced by up to one hundred (100) times. At the bottom 209 of the low volume concentrator 208, excess air, 49.5 liter/minute, is removed from the air flow via an exit port 210. The particles exit the bottom 212 of the low volume concentrator 208 at an airflow output of 0.5 liter/minute in a 0.2 millimeter diameter output stream 210.

FIG. 3 illustrates device 300 used for electrostatic deposition of particles. A tube 302 is attached to the bottom of the electrostatic concentrator device 108. In one embodiment, the tube 302 has a 2 millimeter inner diameter, with a one liter/minute airflow and is spaced two centimeters from the substrate surface. At the bottom of the tube, a corona 304 is formed charging all the exiting particles. The particles are then constricted to a deposition sample having one millimeter or less diameter by a focus electrode 306 operating at −3 Kv bias. A monolayer of particles is then collected on the substrate surface 110.

Figure 4:
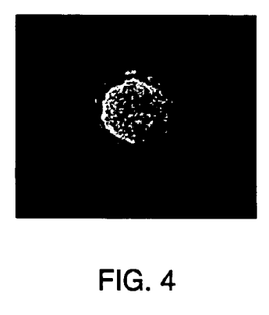

FIG. 4 illustrates an electrostatically deposited sample of particles as described above for device 300.

Figure 5A:
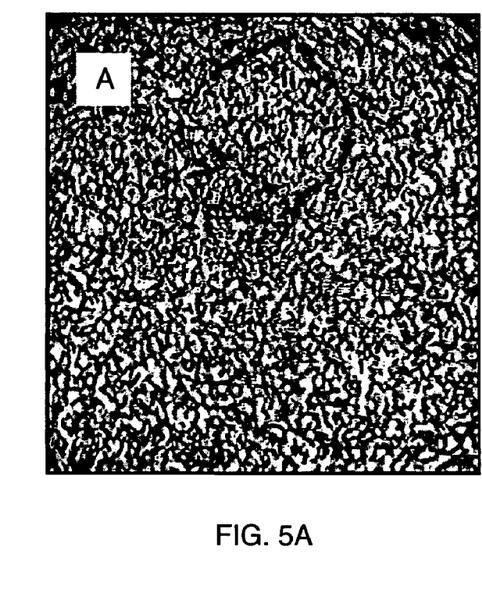
Figure 5B:
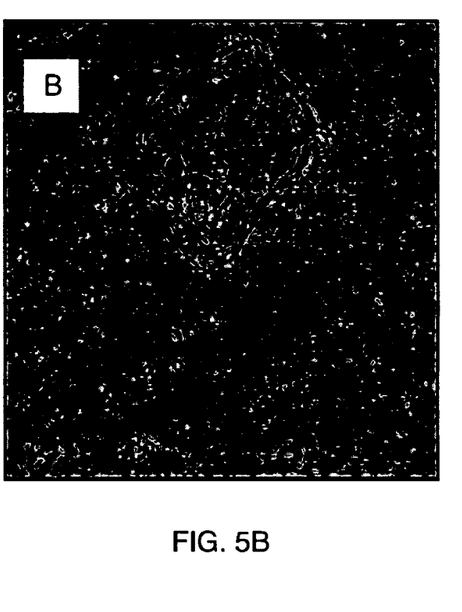
Figure 6A:
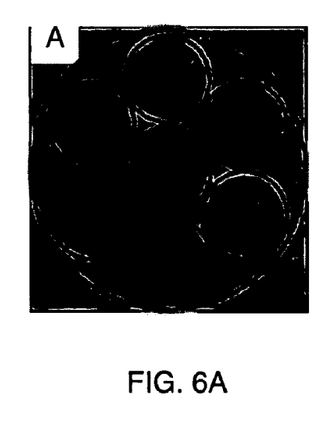
Figure 6B:
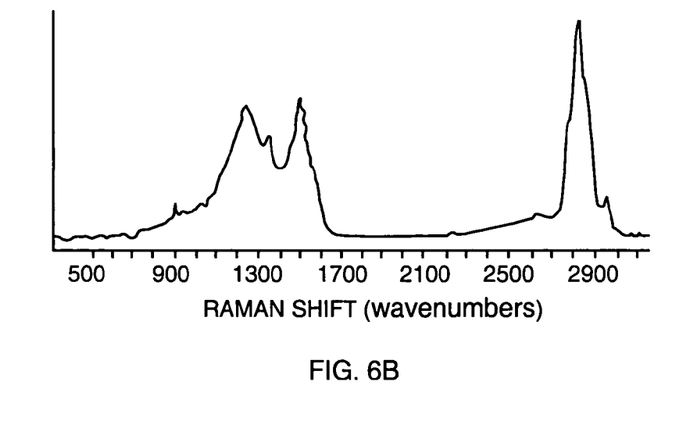
Figure 6C:
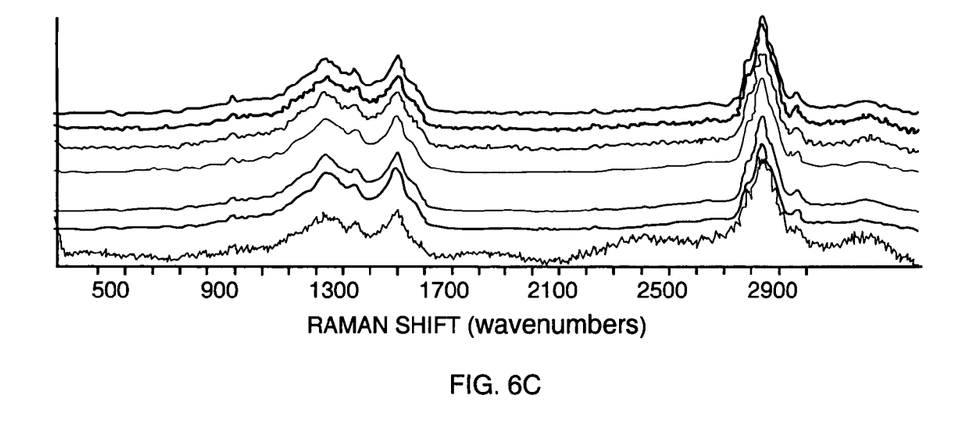
Figure 6D:
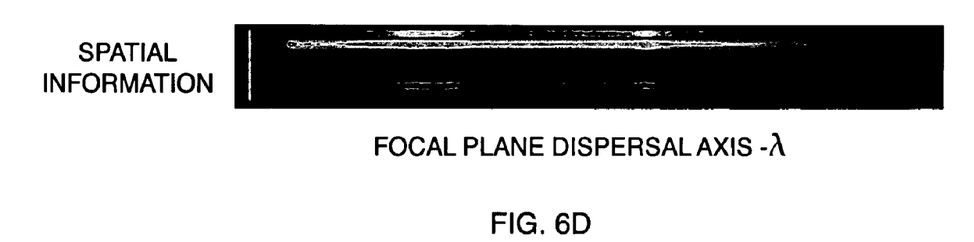

In one embodiment of the present disclosure, the elastic scatter image of the sample is collected on the detector and mode scrambling and frame averaging are used to improve the image contrast by removing the interference pattern of the illumination source producing the final image. FIGS. 5A and 5B illustrate an elastic scatter image of human epithelial cells obtained by one embodiment of the system of the present disclosure. A low power laser source illuminated the sample of human epithelial cells to generate the elastic scatter image of the sample which produces a high cross section elastic scatter image signal. However, the elastic scatter image is typically masked by the presence of a laser interference pattern. The laser interference pattern is removed by mode scrambling and frame averaging. As illustrated in FIG. 5A, the human epithelial cells are not readily observable due to the presence of a laser interference (i.e. speckle) pattern masking the presence of the inherently low contrast cellular object within the field of view of the 20× objective employed to capture the image. As illustrated in FIG. 5B, the cell is readily observable by using a fiber optic to scramble the modes traversing the fiber optic, which effectively makes the monochromatic laser light incoherent. A plurality of images is time averaged and the cellular image contrast is enhanced by effective suppression of the coherent laser speckle pattern. To obtain the image in FIG. 5B, ten images were each collected at 30 frames per second.

In one embodiment, system 100 utilizes an imaging spectrometer 127 in combination with an elastic scatter imaging detector 118 to identify the sample. The elastic scattered photons are imaged by the detector 118 and the Raman scattered photons, produced by the sample are analyzed by an imaging spectrometer 127. The Raman scattered photons are passed through a filter to produce a plurality of spatially resolved spectra.

With reference to FIG. 6, a plurality of Raman spectra were collected on a ChemImage FALCON II Raman microscope from a physical mixture of a sample comprised of ovalbumin ("Ova") and diesel soot ("DS"). The spatially resolved Raman spectra collected from the sample were mapped to the entrance slit of the FALCON II's dispersive Raman spectrometer, using a fiber array spectral translator (FAST). Using FAST, the circular field of view of the image is converted to a curvilinear shape that is mapped to the entrance slit of the spectrometer. The benefits of this approach include rapid collection of the full Raman image spectral hypercube without the need for spatial or spectral scanning mechanisms. Because multiple Raman spectra can be captured within a wide field of view without the need to reposition the laser, fluorescence photo bleaching time can be minimized. In addition, the spatially resolved Raman spectra map the local heterogeneity of the sample mixture which enables target testing based spectral unmixing. As a result, sample mixtures are analyzed in real time if sufficient single to noise reduction is achieved. FIG. 6A illustrates the optical image of Ova/DS under 100× objective magnification. FIG. 6B illustrates a dispersive Raman spectrum representing the average response of the mixture sample, and FIG. 6C illustrates seven spatially resolved dispersive Raman spectra collected from the sample using FAST. FIG. 6D illustrates the dispersive Raman spectral image collected at the focal plane of the spectrometer. The seven independent spatial channels images along the y axis and the Raman spectrum along the x axis of the focal plane are clearly visible.

System 100 also includes a processor 128 that determines the identification of the sample. To identify the sample, the plurality of spatially resolved spectra, produced by the imaging spectrometer, are compared to at least one reference library spectrum to identify the threat agent. In one embodiment, the plurality of spatially resolved Raman spectra are compared to at least one reference Raman library spectrum to identify the threat agent.

In one embodiment, processor 128 utilizes target testing for unmixing signatures and searching the measured mixture spectra relative to the pure component signature library in an automated fashion. Target testing based spectral unmixing compares mixture spectra against pure component library spectra by characterizing the mixture space using principal component analysis ("PCA"); ranking the library spectra by quantifying their goodness of fit into the mixture data space; and determining by target testing the number and identity of the pure spectra present in the mixture sample.

With further reference to FIG. 6, the sample was classified as diesel soot using a Euclidian Distance (ED) matched filter identifier algorithm. The ED algorithm assumes samples are pure components, which was an inaccurate assumption. When the spatially resolved dispersive Raman spectra are analyzed using a target testing spectral unmixing algorithm, the mixture sample was correctly classified as being comprised of Ova and carbonaceous material, a material class comprised of DS and humic acid, because of their Raman spectral similarity.

The target testing algorithm includes the following general steps:

1. Use PCA on the mixture spectra to characterize the mixture data space.
2. Calculate the angle of projection of each library spectrum with the mixture data space. A dot product of a vector with an n-dimensional space. A dot product of 1.0 represents a perfect fit into the data space.
3. Rank all library spectra by the angle of projection into the mixture data space.
4. Consider all permutations of the top matches as ranked by angle. Determine the n most likely candidate pure components. Generate all possible m component solutions, where m varies from 1 to n and is the number of library spectra in a given solution.
5. For each candidate solution calculate the correlation coefficient; calculate projected library spectra for each set of m component library spectra (given the known mixture spectra and the known library spectra). Calculate the correlation coefficient of each projected library spectrum with the actual library spectrum. The correlation coefficient used as the selection criterion is the square root of the sum of squares of the dot products for each member of a given m component solution.
6. The most probable solution is the one with the highest correlation coefficient.

The target testing algorithm requires a Raman signature library that supports differentiation between threat agents, near neighbors, and clutter independent of agent growth or preparation conditions and sample history. Raman spectra of threat agents include certain spectral brands that are highly sensitive to growth conditions and others that are relatively insensitive to growth conditions. The detection and identification algorithms will focus on spectral bands that maximize agent discrimination, but minimize sensitivity to growth conditions can minimize signature library dependence on unwanted biological contributions to variability.

Figure 1:
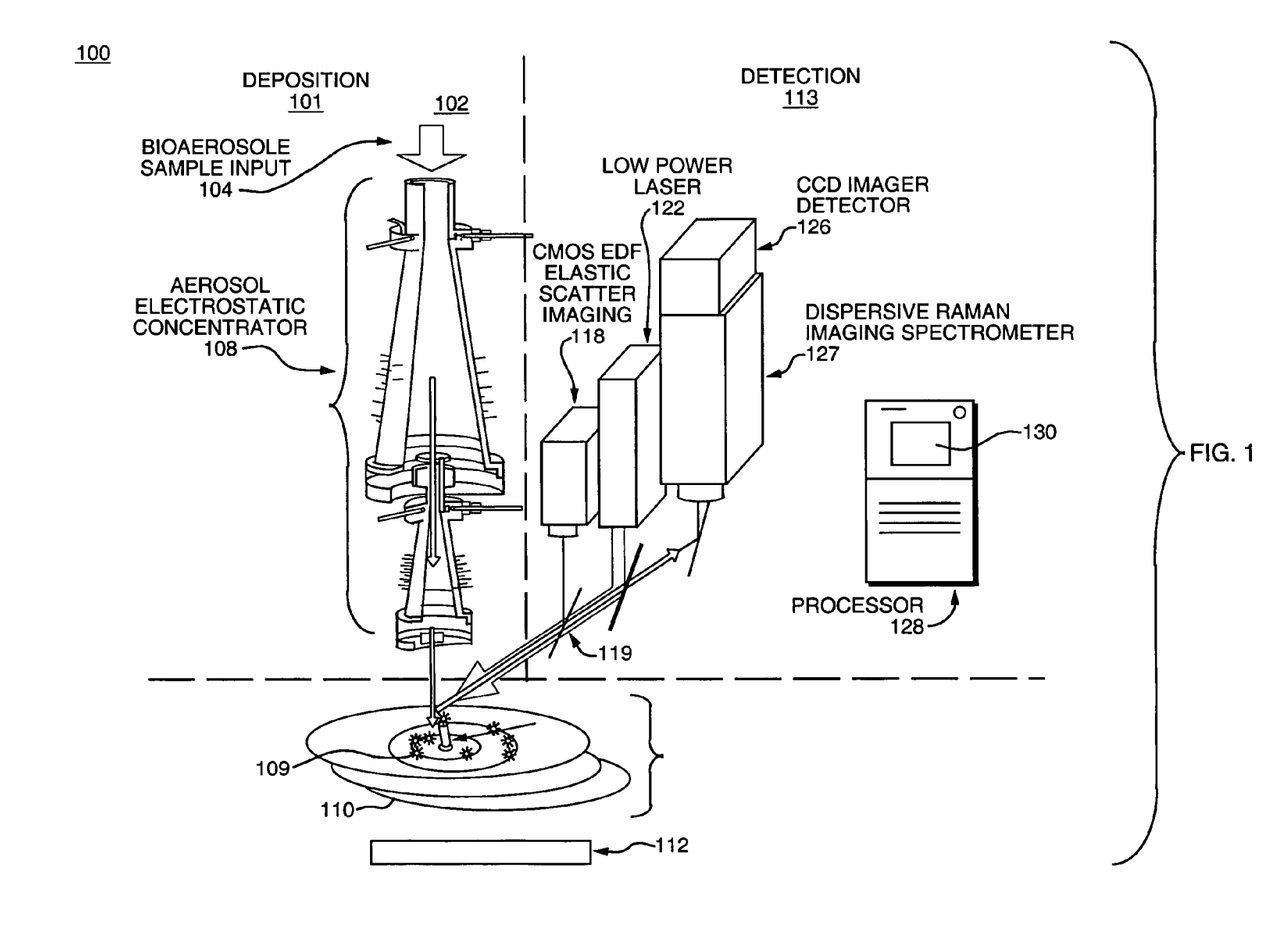
Figure 2:
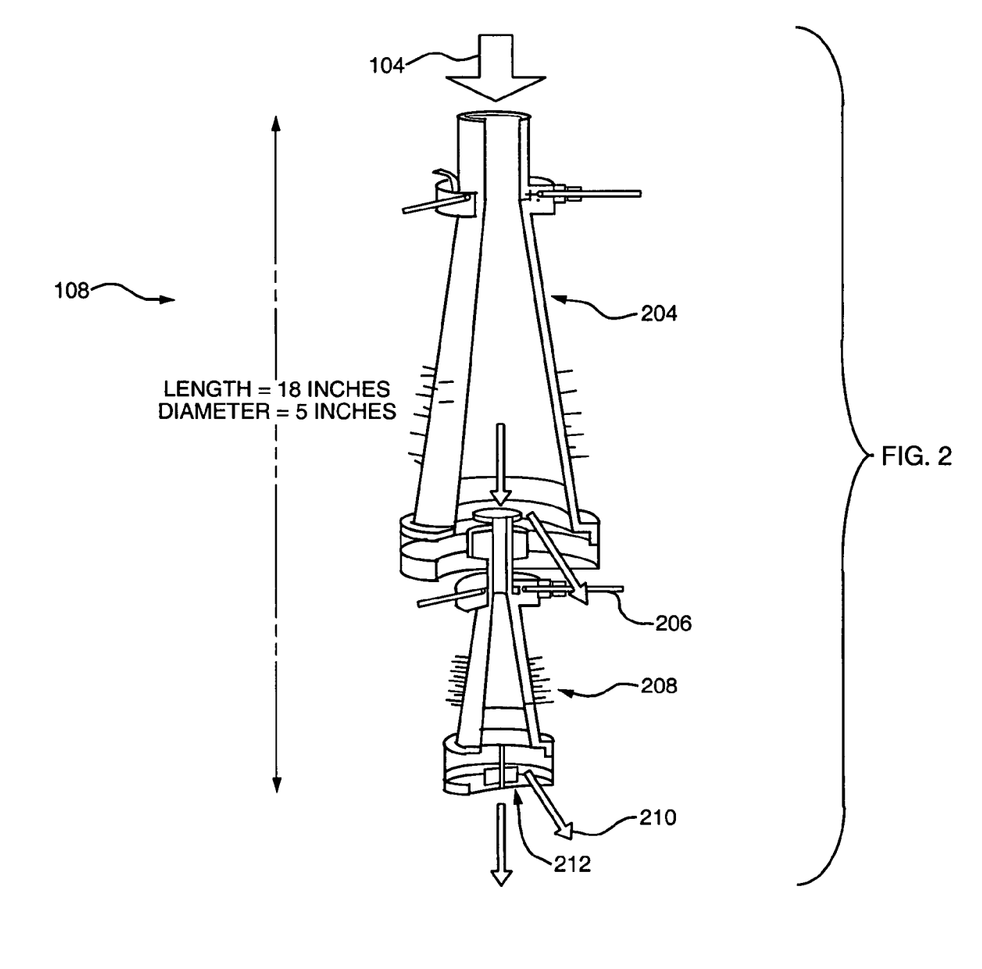
Figure 3:
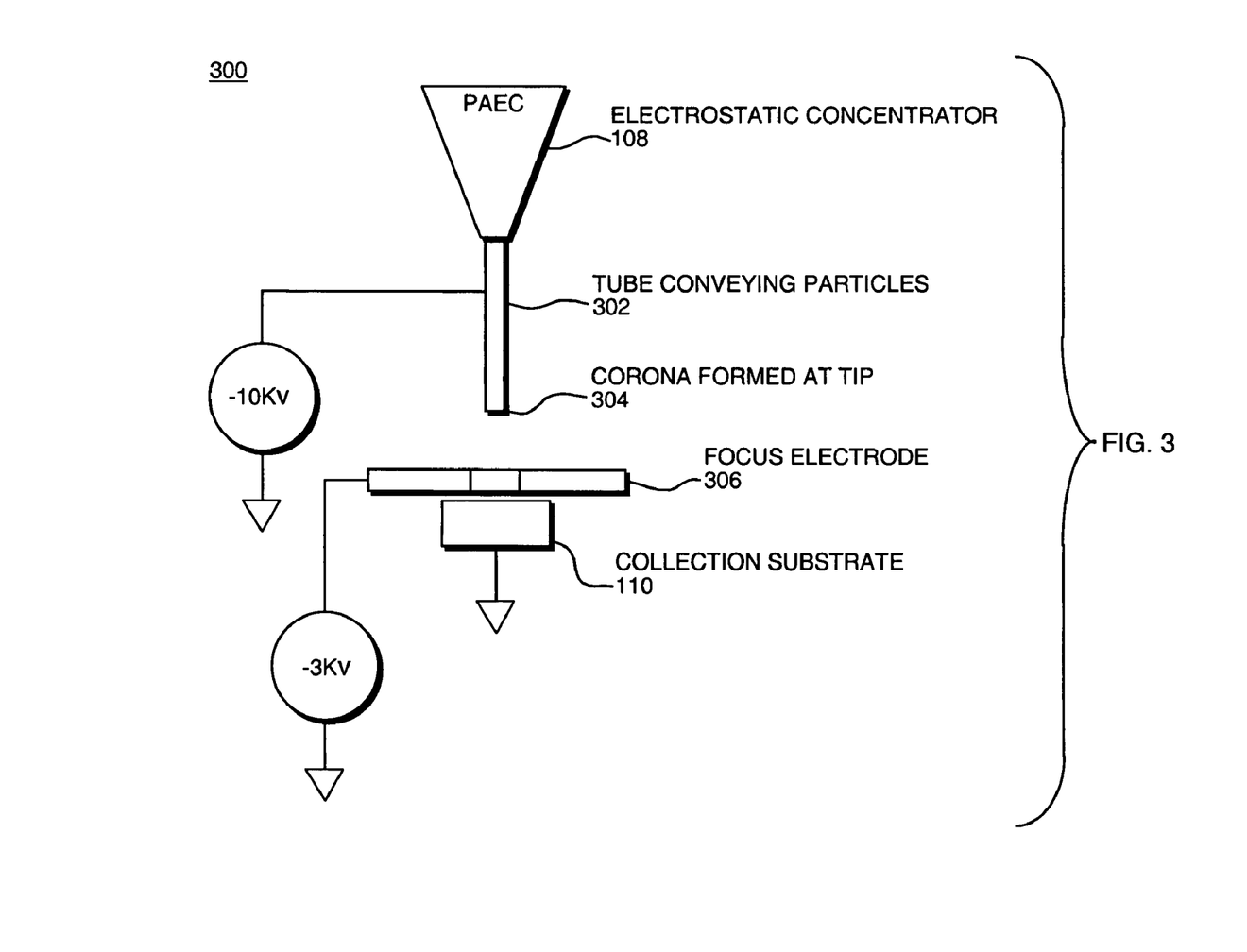

With further reference to FIG. 1, system 100 includes a deposition substrate 110 and substrate positioning mechanism 112. The substrate 110 provides for the deposition of a plurality of samples at predetermined sites. The substrate 110 includes a compact disk ("CD") configuration or any similar circular or non-circular, substantially flat surface of metal or non-metal. In one embodiment, the deposition substrate 110 is conductive serving as an electrode in the deposition circuitry. The substrate 110 is made from materials including aluminum-coated glass, ceramic, or polycarbonate disks, native and metallized silicon wafers, and machine ground metal plates. The substrate 110 is to enable autonomous focusing of the Raman laser on the substrate. In one embodiment, the substrate includes a standard audio CD dimensions for the substrate allowing for collection of approximately 1,800 samples on a standard 120 mm diameter CD. System 100 also includes storage unit capable of holding 25 substrates to support 30 days worth of sampling, 43,800 samples collected in 30 days@1,800 samples per substrate. The concept is for the substrate-disks to be supplied in a cartridge that can be easily swapped out after 30 days of operation. The storage system includes a marking technique to log the archived samples for conditions at the point of data collection e.g., time, date, sensor settings, and for sample relocation. The substrate positioning device 112 includes a motion stage having two degrees of freedom, directional linear motion and rotationally variable. The motion of the substrate positioning device 112 generates sample deposits in spiral tracks, circular concentric tracks, or in linear tracks. The substrates are stored in a storage system designed to protect the resilience of the deposition spots to mechanical shock/vibration, humidity, and other physicochemical agents that might degrade their stability.

The present disclosure may be embodied in other specific forms without departing from the spirit or essential attributes of the disclosure. Accordingly, reference should be made to the appended claims, rather than the foregoing specification, as indicated the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:

1. A method, comprising:

using electrostatic deposition for collecting and concentrating particles into a collimated, low flow air steam and to deposit a sample of a threat agent onto a substrate;

illuminating the threat agent deposited on the substrate with a plurality of photons to thereby produce Raman scattered photons; and analyzing the Raman scattered photons in order to identify the threat agent;

analyzing elastic scattered photons, produced by the threat agent on the substrate, using elastic scattering imaging to form an image of the threat agent.

2. The method of claim 1, further comprising comparing Raman spectrum to at least one reference Raman library spectrum to identify the threat agent.

3. The method of claim 1, wherein analyzing the Raman scattered photons further comprises generating multiple spatially independent image channels anywhere within a Raman shift of about 0 $cm^{-1}$ to about 3500 $cm^{-1}$ at a full spectral resolution less than 20 $cm^{-1}$.

4. The method of claim 1, wherein analyzing the elastic scattered photons produced by the threat agent comprises automatically focusing the image of the threat agent on the substrate using one of the following: a CMOS detector, a CCD detector or a high frame rate digital detector, in combination with a feedback control mechanism.

5. A system, comprising:

an electrostatic device for collecting and concentrating particles into a collimated, low flow air steam and for depositing a sample of a threat agent into a substrate;

an illumination source to illuminate the threat agent deposited onto the substrate with a plurality of photons to thereby produce Raman scattered photons;

a means for analyzing the Raman scattered photons in order to identify the threat agent; and a means for analyzing elastic scattered photons, produced by the threat agent on the substrate, using elastic scattering imaging to form an image of the threat agent.

* * * * *